United States Patent [19]

Shatkina et al.

[11] Patent Number: 4,911,925

[45] Date of Patent: Mar. 27, 1990

[54] VEGETABLE EXTRACTS FOR SKIN TREATMENT

[76] Inventors: Lima Shatkina; Rubina Shatkina, both of 26-85 University Ave., The Bronx, N.Y. 10468

[21] Appl. No.: 339,093

[22] Filed: Apr. 17, 1989

[51] Int. Cl.$^4$ ............................................... A61K 7/48
[52] U.S. Cl. ..................... 424/401; 424/658; 424/195.1; 424/659; 514/783; 514/844; 514/845; 514/846; 514/847; 514/848
[58] Field of Search ..................... 424/401, 195.1, 658, 424/659; 514/783, 844, 845, 846, 847, 848

[56] References Cited

U.S. PATENT DOCUMENTS

| | | | |
|---|---|---|---|
| 2,566,722 | 9/1951 | Friedberg | 424/401 |
| 4,165,385 | 8/1979 | LeFebvre | 514/783 |
| 4,581,230 | 4/1986 | Grollier et al. | 424/195.1 |
| 4,614,652 | 9/1986 | Vályi et al. | 424/195.1 |
| 4,737,360 | 4/1988 | Allen et al. | 514/844 |
| 4,746,510 | 5/1988 | Grollier et al. | 424/195.1 |
| 4,767,618 | 8/1988 | Grollier et al. | 424/195.1 |

*Primary Examiner*—Thurman K. Page
*Assistant Examiner*—James M. Spear
*Attorney, Agent, or Firm*—Ilya Zborovsky

[57] ABSTRACT

A substance for treatment of skin includes a fatty base of natural animal and vegetable oils and an aqueous extract of herbs.

1 Claim, No Drawings

VEGETABLE EXTRACTS FOR SKIN TREATMENT

BACKGROUND OF THE INVENTION

The present invention relates to skin treatment substances.

Skin treatment substances or creams are widely known and used. One of the most important problems of modern cosmetology is preventing or delay of skin aging and a search for means for stimulating skin activity to prevent deterioration of skin, reduction of its strength and development and of wrinkles. One of the symptoms of skin aging is hysteresis of protoplasm, change in colloidal condition of proteins which form the tissue, decrease of water and fat contents of the skin. This leads to slowing down of biological and biophysical reactions and moveability of dissolved components, reduction of oxygen consumption, decrease of main metabolic processes. Especially in these cases the use of fats in substances for preventing wrinkles formation and premature fading of skin is of great importance, utilized together with water in forms which are optimal for absorption and retention by skin.

Known skin treatment substances or creams which are now produced have a vaseline base, sometimes with a small addition of animal and plant fats have considerable advantages, in their low cost, non-oxidation by air, stability of consistency during storage, etc. However, they also negatively affect the skin. Vaselines cannot replace in their action the animal and plant fats. They soften the skin only insignificantly and act only on the skin surface and prevent penetration of nutrient and medicinal substances needed for the skin. Moreover, long use of creams frequently lead to skin sicknesses.

In modern cosmetology also creams comprising hormones such as for example estrogen, placenta, etc. have been used. Very small dosages of hormones are harmless, but at the same time not efficient. Therefore, the hormone-containing creams include a considerable quantity of hormones and as a result are dangerous for organism. Estrogen applied on the skin penetrates into the organism and can lead to cancer. Hormone-containing creams can lead to hair growth and other side effects. Auxiliary components used in known creams increase their costs, however frequently they do not improve the results and sometimes dry the skin.

SUMMARY OF THE INVENTION

Accordingly, it is an object of the present invention to provide a skin treatment substance which avoids the disadvantages of the prior art.

In keeping with these objects and with others which will become apparent hereinafter, one feature of the present invention resides, briefly stated, in a skin treatment substance which includes a fatty part composed only of natural oils, and an aqueous vegetable extract of several herbs, with the fatty part preferably 50-40 weight parts and the vegetable extract preferably 40-20 weight parts.

When the substance is made in accordance with the present invention it avoids the disadvantages of the prior art as will be explained hereinbelow.

The novel features of the present invention are set forth in the appended claims. The invention itself, however, will be best understood from the following description of preferred embodiments.

DESCRIPTION OF PREFFERED EMBODIMENTS

A substance for treatment of skin in accordance with the present invention includes the following conponents (in weight parts):

| | |
|---|---|
| Lanoline anhydrous | 20-15 |
| spermaceti | 12-10 |
| cocoa-butter | 10-5 |
| bees wax | 7-5 |
| mixture of substantially equal parts of olive and corn oils | 50-40 |
| vegetable aqueous extract | 40-20 |
| borax | 1 g per 100 ml of the extract |
| boric acid | 1 g per 100 ml of the extract |
| citric acid | 1-3 g per 100 ml of the extract |

The vegetable extract presented hereinabove includes the following medicinal vegetables or herbs:

*Flores calendulae*
*Chrysanthemum chamomilla*
*Hypericum perforatum L*
*Achillea millefolium.*

The above vegetables in the extract are taken in substantially equal parts.

The skin treatment substance in accordance with the present invention is prepared in the following manner:

All components, with the exception of vegetable extract are melted on water bath with continuous mixing. Then the hot vegetable aqueous extract with the preliminarily dissolved borax, boric and citric acids is introduced into the liquified melted part of the cream. The thus produced mixture is being mixed, gradually cooled and rigidified during 15-20 min in freezer chamber of a refrigerator. The above procedure of melting on the water bath with mixing, and subsequent cooling with continuing mixing is repeated three times. Then the substance is ready to use.

The vegetable extract is prepared in the following manner. 10-20 grams of a large grain mixture of dry vegetables is introduced into 200 ml of boiling water and left for 20 min. Then the extract is sieved, borax, boric and citric acids are dissolved in it, and the extract in hot condition with continuous mixing is introduced into hot liquid main part of the cream.

The inventive skin treatment substance can be applied on a preliminarily cleaned skin of face or neck with a thin layer, as well as onto the skin of forehead along its middle line, chin, neck. Then with tender movements without displacement of the skin the cream is spread along whole face and neck. It is left for 2-3 hours (depending on the skin sensitivity). Then it can be removed with paper napkins or tissues. It is not recommended to leave the cream on for a whole night.

The invention is not limited to the details shown since various modifications and structural changes are possible without departing in any way from the spirit of the invention.

The skin treatment substance of the invention is especially recommended for treatment of aging skin to increase its breathing ability, regulate oxidative processes in skin, effect positively blood circulation in skin, improve regenerative/reproductive ability of skin, activate metabolism.

The substances are rapidly absorbed in skin, makes it soft and tender, preserves its elasticity, increases its resiliency, narrows the surface skin vessels and does not cause irritations. Its fatty base has a high specific activity. It exceeds other fats and fatty substances. It softens the skin, makes it velvet-like, increases its resiliency, causes blood flow and activates skin metabolism. It also penetrates into deep skin layers and introduces nutrient and medicinal components into them.

The vegetable extract is of a paramount importance. It is a highly efficient medical substance which possesses bactericidal/antiseptic and antiinflammation properties. It removes irritations of skin. It has a high quantity of vitamins and therefore improves the skin reducing its flabbiness, sluggishness, smoothes the wrinkles and delays premature aging of skin. It also contributes to metabolism of skin, accelerates and facilitates the processes of assimilation of nutrient products by the skin which products are supplied by blood. Therefore it increases the skin tone and vitality.

What is desired to be protected by Letters Patent is set forth in particular in the appended claims.

We claim:
1. A substance for treatment of skin, comprising in weight parts:
   lanoline anhydrous: 20-15
   spermaceti: 12-10
   cocoa butter: 10-5
   bees wax: 7-5
   mixture of substantially equal parts of olive and corn oils: 50-40
   vegetable aqueous extract: 40-20
   borax: 1 g per 100 ml of extract
   boric.acid: 1 g per 100 ml of extract
   citric acid: 1-3 g per 100 ml of extract,
wherein the extract contains substantially equal weight parts of
   *Flores calendulae*
   Chrysanthemum chamomilla
   Hypericum perforatum L
   Achillea millefolium.

* * * * *